United States Patent
Franks

[19]

[11] Patent Number: 5,983,991
[45] Date of Patent: Nov. 16, 1999

[54] TISSUE CHUCK

[76] Inventor: James W. Franks, 2153 Driftwood Cir., Palm Beach Gardens, Fla. 33410

[21] Appl. No.: 08/885,221

[22] Filed: Jun. 30, 1997

[51] Int. Cl.$^6$ ...................................................... F28F 7/00
[52] U.S. Cl. .......................... 165/80.1; 165/168; 165/185; 269/7
[58] Field of Search .................................. 165/80.1, 170, 165/168, 185; 269/7; 83/170

[56] References Cited

U.S. PATENT DOCUMENTS

| | | | |
|---|---|---|---|
| 1,413,571 | 4/1922 | Bronander | 165/170 |
| 2,629,230 | 2/1953 | Turner | 269/7 X |
| 3,218,896 | 11/1965 | McCormick | 269/7 X |
| 3,361,019 | 1/1968 | Weiskopf | 269/7 X |
| 3,574,257 | 4/1971 | Du Bois et al. | 269/7 X |
| 3,823,771 | 7/1974 | Ludwig | 165/168 X |
| 5,000,254 | 3/1991 | Williams | 165/185 X |

FOREIGN PATENT DOCUMENTS

| | | | |
|---|---|---|---|
| 1353594 | 1/1964 | France | 165/168 |
| 787865 | 12/1980 | U.S.S.R. | 165/170 |
| 1179084 | 9/1985 | U.S.S.R. | 165/170 |

*Primary Examiner*—Leonard Leo

[57] ABSTRACT

A tissue chuck for use with a chuck holder for preparing a tissue sample for sectioning in a cryostat or the like, includes a base, having a tissue mounting surface and a heat transfer surface, and a plurality of fins for transferring heat from the heat transfer surface. Each fin terminates in a fin end, and each fin end is in spaced relation to the base.

4 Claims, 8 Drawing Sheets

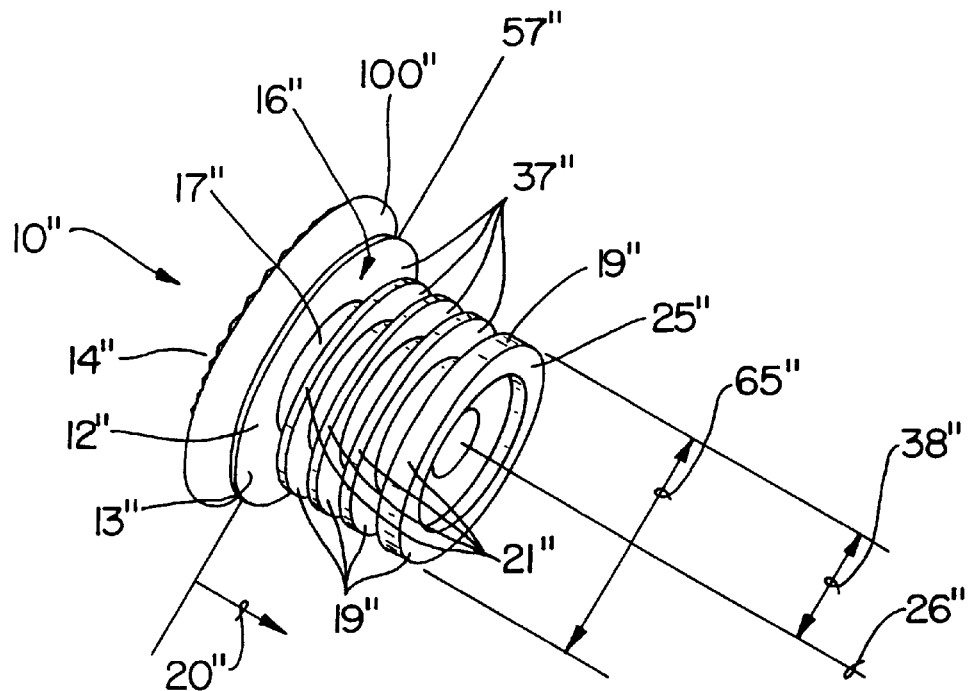
FIG. 8
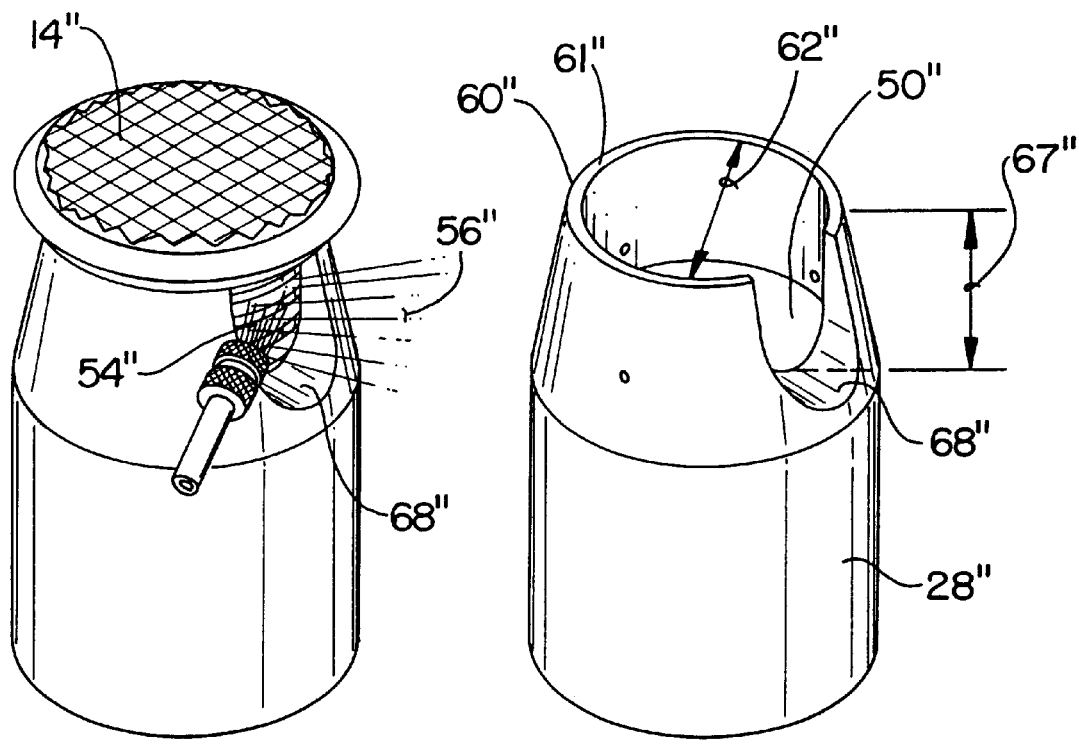
FIG. 10
FIG. 9

TISSUE CHUCK

DESCRIPTION

1. Technical Field

This invention relates to the preparation of tissue samples for sectioning, and specifically to chucks used to hold tissue in the preparation of samples prior to frozen sectioning of that tissue.

2. Background Art

The Mohs tissue surgical technique, which was developed by Frederic E. Mohs of Madison, Wis., is a method of removing skin tumors such as cutaneous malignancies and certain major carcinomas, and evaluating sections (very thin slices) of the tissue under a microscope. To obtain these sections, a tissue sample must be sliced by a device known in the art as a microtome. The microtome is typically located in a refrigerated unit, called a cryostat, which is capable of maintaining an internal temperature of −20 degrees Celsius or below.

Prior to this sectioning or slicing, the tissue must be mounted on a cryostat chuck. A procedure typically used to mount the tissue sample to a tissue chuck includes placing the tissue sample and a small amount of viscous embedding material such as O.C.T. fluid (a tissue mounting fluid such as this is sold under the brand name Tissue Tek II O.C.T. Compound, by Miles Laboratories, Inc.) onto the tissue mounting surface of the chuck, and cooling the O.C.T. and tissue sample until they freeze solid to the chuck. The chuck and attached tissue sample are then placed into a chuck fixture in the cryostat where the tissue is cut into frozen sections having a thickness of only five to seven micrometers. Each section is then placed on a microscope slide and the section is processed and evaluated by techniques that are well known in the art.

One well known method of freezing the O.C.T. and tissue sample involves placing the chuck, which is typically made of a material having high thermal conductivity such as brass or aluminum, within the cryostat and cooling the chuck to −20 degrees Celsius ("C."). A small puddle of O.C.T. is then placed on the mounting surface of the chuck, and the tissue sample is positioned into the puddle. A heat sink (typically a small mass of brass) also at −20 degrees C., may be lowered onto the O.C.T. and tissue sample to flatten the tissue and accelerate the freezing process. Unfortunately, this inexact method requires the technician or surgeon to manipulate the O.C.T. container and tissue sample obscured by the heat sink, within the confines of the cryostat while their hands are exposed to the −20 degree C. temperature that is maintained therein. Such a method is like ironing a wrinkled shirt, blindly, with a concrete block. Additionally, such manipulation can be dangerous due to the close proximity of the knife that is part of the microtome.

To avoid these problems, another method used by many practitioners involves freezing the O.C.T. and tissue sample to the chuck while the chuck is outside of the cryostat. In this method, the O.C.T. and tissue sample are placed on the mounting surface of the chuck, and then the O.C.T. and tissue sample are sprayed with liquid nitrogen or compressed carbon dioxide until frozen. One of the disadvantages of this procedure is that, as the O.C.T. is sprayed with such cold gas, the gas tends to splatter the O.C.T. off the mounting surface of the chuck. Not only may this require additional clean-up of the chuck and surrounding work area, but if too much O.C.T. is splattered from the mounting surface of the chuck, the remaining O.C.T. may be insufficient to properly support the tissue sample during slicing thereof in the cryostat. Additionally, spraying liquid nitrogen directly on the O.C.T. may cause small bubbles of nitrogen to form in the liquid O.C.T. as some of the liquid nitrogen breaks through the surface of the O.C.T. This may cause the tissue sample to be held less firmly on completion of freezing than if no nitrogen had intruded into the O.C.T.

To avoid splattering the O.C.T., the nitrogen can be sprayed onto the O.C.T. and tissue sample in lighter bursts, or at a greater distance, until the outer surface of the O.C.T. forms a shell. Then the nitrogen can be sprayed more directly onto the O.C.T. to complete the freezing process. While this method prevents splattering the O.C.T., it is a method that consumes both time and excessive amounts of liquid nitrogen. Further, between bursts of liquid nitrogen, moisture from the air is able to condense on the O.C.T., creating a frost layer on the outer surface that tends to insulate the O.C.T. from further cooling (since the frost also forms on the tissue sample, the tissue sample is obscured and cannot be viewed directly, and any anomaly which may occur to the tissue sample during the freezing process may go undetected). As a result, this method avoids the problem of O.C.T. splattering at the expense of consuming significantly greater amounts of liquid nitrogen, which in turn increases the likelihood that the technician will run out of liquid nitrogen, thereby interrupting the tissue mounting procedure and requiring the procedure to be started over.

What is needed is a tissue chuck that aids in the freezing of tissue samples while providing complete visualization without the problems inherent in working within the confines of a cryostat, or spraying coolant directly on the tissue sample and O.C.T.

SUMMARY OF THE INVENTION

It is therefore an object of the present invention to provide a tissue chuck to which the O.C.T. and tissue sample can be frozen outside of a cryostat without the necessity of resorting to the time consuming methods of the prior art to avoid splattering the O.C.T.

Accordingly, to the present invention is a tissue chuck for use with a chuck holder for preparing a tissue sample for sectioning in a cryostat or the like, and includes a base, having a tissue mounting surface and a heat transfer surface, and a plurality of fins for transferring heat from the heat transfer surface. Each fin terminates in a fin end, and each fin end is in spaced relation to the base.

The foregoing and other features and advantages of the present invention will become more apparent from the following description and accompanying drawings.

BRIEF DESCRIPTION OF THE DRAWINGS

FIG. 8 is a perspective view of the first alternate embodiment of the tissue chuck of the present invention.

FIG. 9 is a view of a chuck holder for use with the first alternate embodiment.

FIG. 10 is a perspective view of the chuck and chuck holder of FIGS. 8 and 9; showing the introduction of coolant into the channels of the first alternate embodiment of the present invention.

BEST MODE FOR CARRYING OUT THE INVENTION

Figure 1:
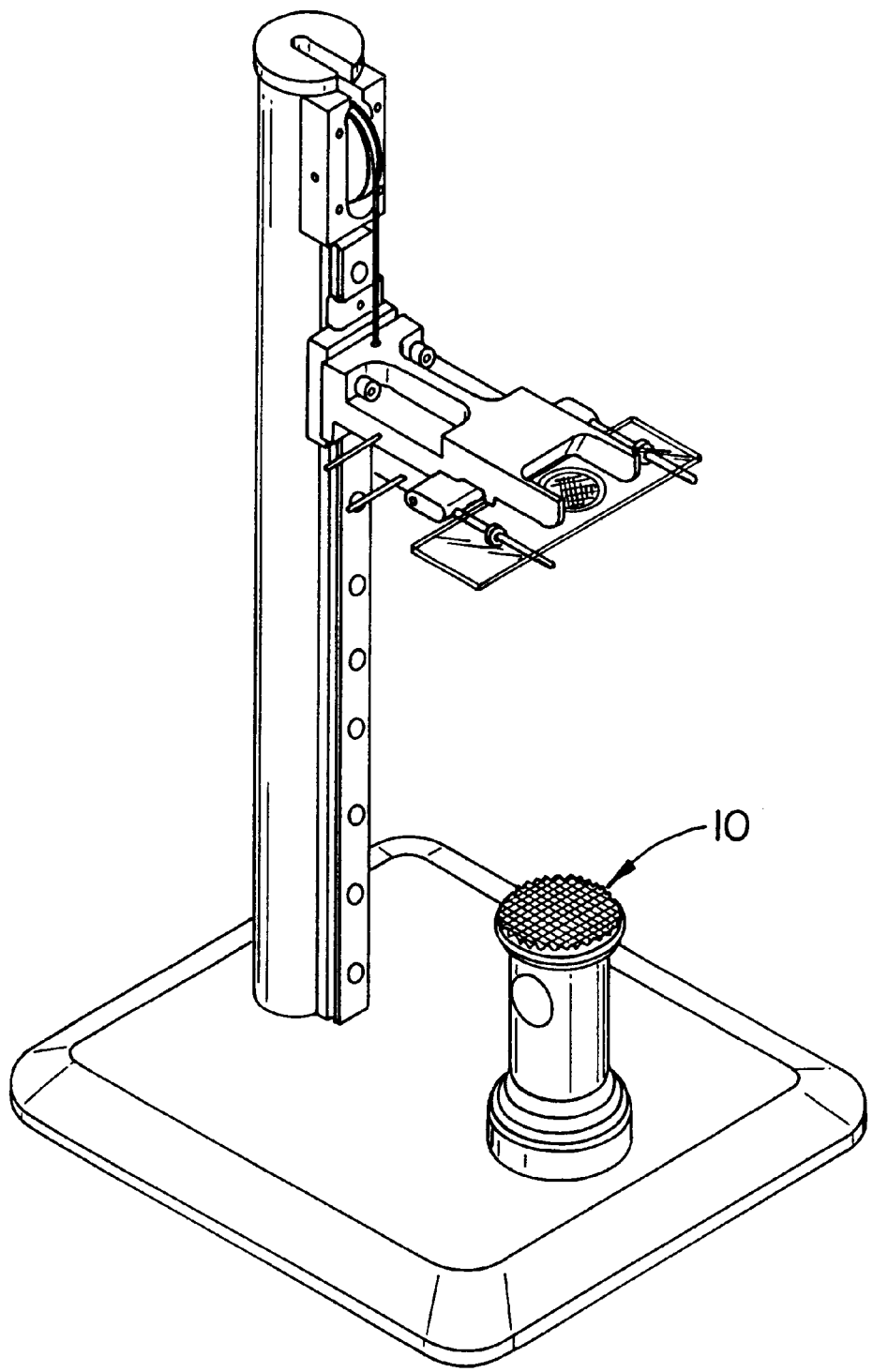
FIG. 1 is a perspective view of an apparatus with which the present invention can be used.
Figure 2:
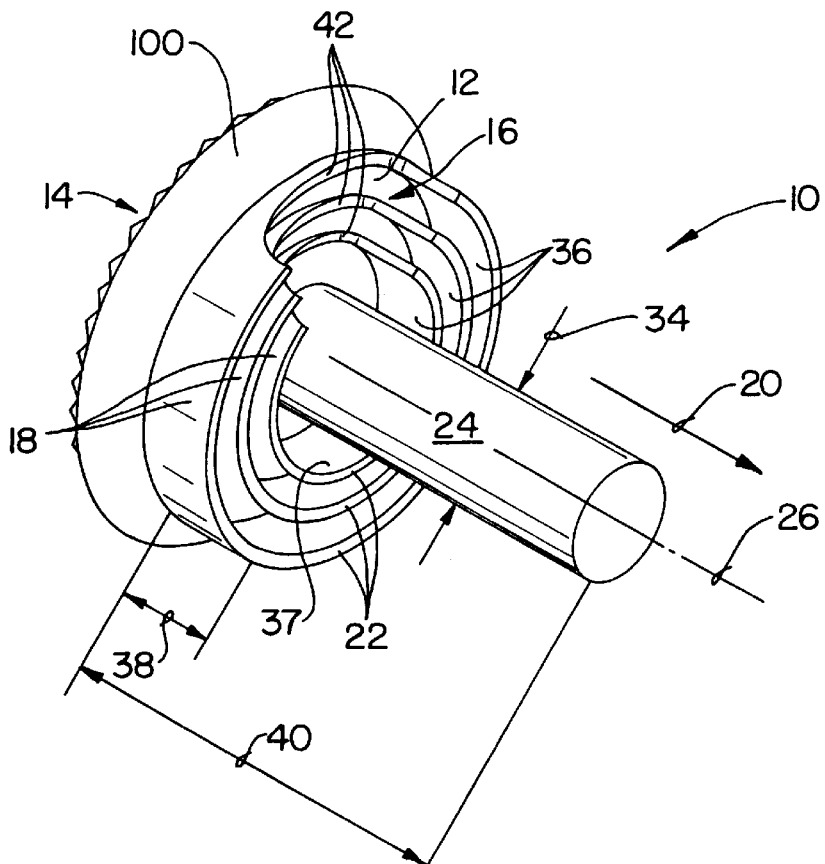
FIG. 2 is a perspective view of a first embodiment of the present invention.

The tissue chuck 10 of the present invention is suitable for use with a variety of devices used in the Mohs tissue surgical technique, including the tissue mounting apparatus shown in FIG. 1. The tissue chuck 10 of the present invention as shown in FIG. 2 includes a base 12 having a tissue mounting surface 14 and a heat transfer surface 16. The chuck 10 is preferably made of a material having high thermal conductivity, such as aluminum. Integral with the heat transfer surface 16 is a plurality of fins 18 extending in a first direction 20 away from the heat transfer surface 16. Each fin 18 terminates in a fin end 22, and each fin end 22 is in spaced relation to the base 12.

Figure 3:
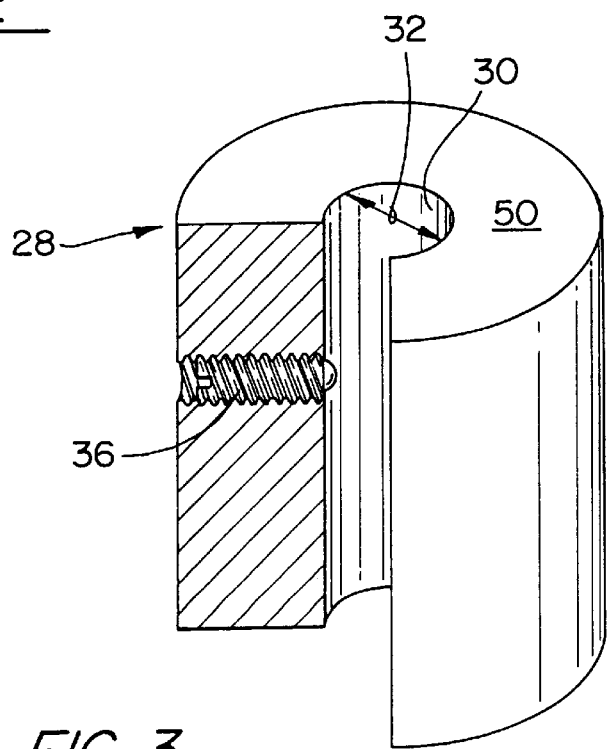
FIG. 3 is a partially sectioned view of a chuck holder for use with the first embodiment.

A post 24 that is integral with the base 12 extends in the first direction away from the base 12 along a reference axis 26. The post 24, which is in spaced relation to each of the fins 18 and is preferably cylindrical, provides the means for removeably securing the chuck 10 to the chuck holder 28. As shown in FIG. 3, the chuck holder 28 comprises a piece of solid material, preferably a hard plastic, having a bore 30 extending vertically therethrough and a planar upper surface 50. The bore 30 has a diameter 32 that is only slightly larger than the diameter 34 of the post 24 to provide a snug fit between the chuck holder 28 and the post 24 of the tissue chuck 10. Preferably, the chuck holder 28 includes a spring loaded set screw 36 to maintain a snug fit between the chuck holder 28 and the post 24 of the tissue chuck 10 despite differences in thermal expansion between the post 24 and the chuck holder 28.

Referring again to FIG. 2, the base 12 is substantially circular and has an O-ring 100 seated in a groove (not shown) that extends about the circumference thereof. Each fin 18 is annular and coaxial with the reference axis 26, and each fin 18 is in spaced relation to each adjacent fin 18, thereby defining channels 36 therebetween, and between the post 24 and the radially innermost fin 37. Each of the fins 18 is coaxial with the post 24, and each fin 18 extends a first predetermined distance 38 from the base 12. The post 24 extends a second predetermined distance 40 from the base 12, and the second predetermined distance 40 is at least twice the first predetermined distance 38. Preferably, each of the fins 18 includes a first cut-out 42, and the first cut-out 42 of each fin 18 is radially aligned with the first cut-out 42 of each of the other fins 18 relative to the reference axis 26.

Figure 4:
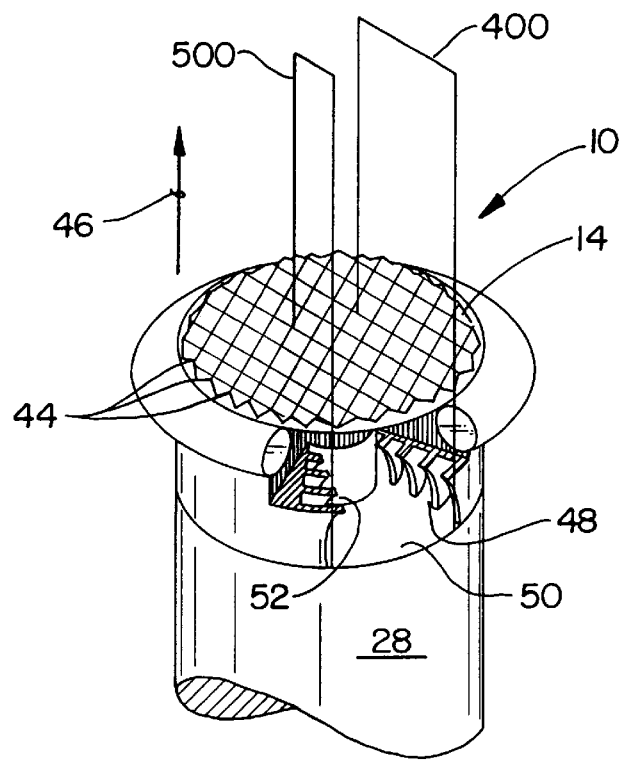
FIG. 4 is a perspective view of the first embodiment of the present invention positioned within a chuck holder.

Referring to FIG. 4, the tissue mounting surface 14 comprises a substantially planar surface having a plurality of protrusions 44 extending therefrom in a second direction 46 opposite the first direction 20. Since each of the fins 18 extends the same distance 38 from the base 12, each of the fins 18 rests on the upper surface 50 when the chuck 10 is positioned into the chuck holder 28, such that the only inlets 48 and outlets 52 for each of the channels 36 occur at the first cut-out 42. Preferably, the inlets 48 are coplanar with a first reference plane 500, the outlets 52 are coplanar with a second reference plane 400, and the reference axis 26 defines the intersection of the first and second reference planes 500, 400.

Figure 5:
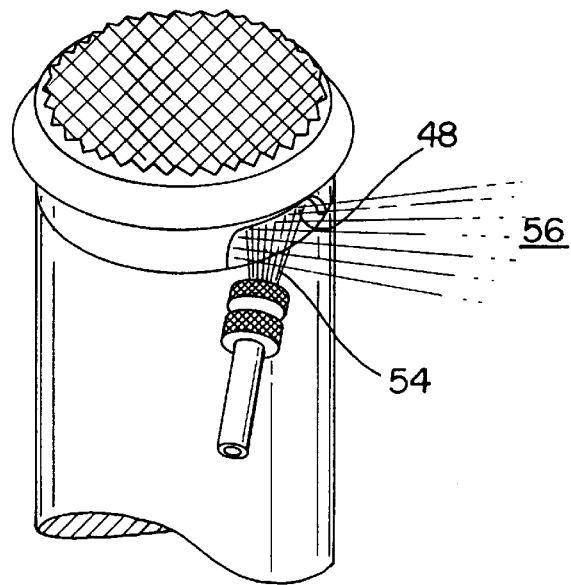
FIG. 5 is the perspective view of FIG. 4, showing the introduction of coolant into the inlets of the channels of the first embodiment of the present invention.

As shown in FIG. 5, when coolant 54, such as liquid nitrogen, is sprayed into the first-cut-outs 42 at an angle that directs the coolant predominantly into the inlets 48, coolant 54 flows through each channel 36 to the outlet 52 and exits the chuck 10 as exhaust 56. As those skilled in the art will readily appreciate as the coolant 54 passes through the channels 36, the coolant 54 absorbs heat from the fins 18 which in turn conduct heat from the tissue mounting surface 14 of the base 12. This causes rapid cooling of tissue mounting surface 14 at a rate which is sufficient to freeze the O.C.T. and tissue sample in a matter of seconds (complete cooling of the chuck, O.C.T. and tissue sample to sub-freezing temperature is typically achieved in 8 to 18 seconds, depending on the chuck design). This freezing is achieved without having to spray coolant directly onto the tissue sample (not shown). Thus, the problems associated with spraying coolant directly of the tissue sample are avoided entirely.

Figure 6:
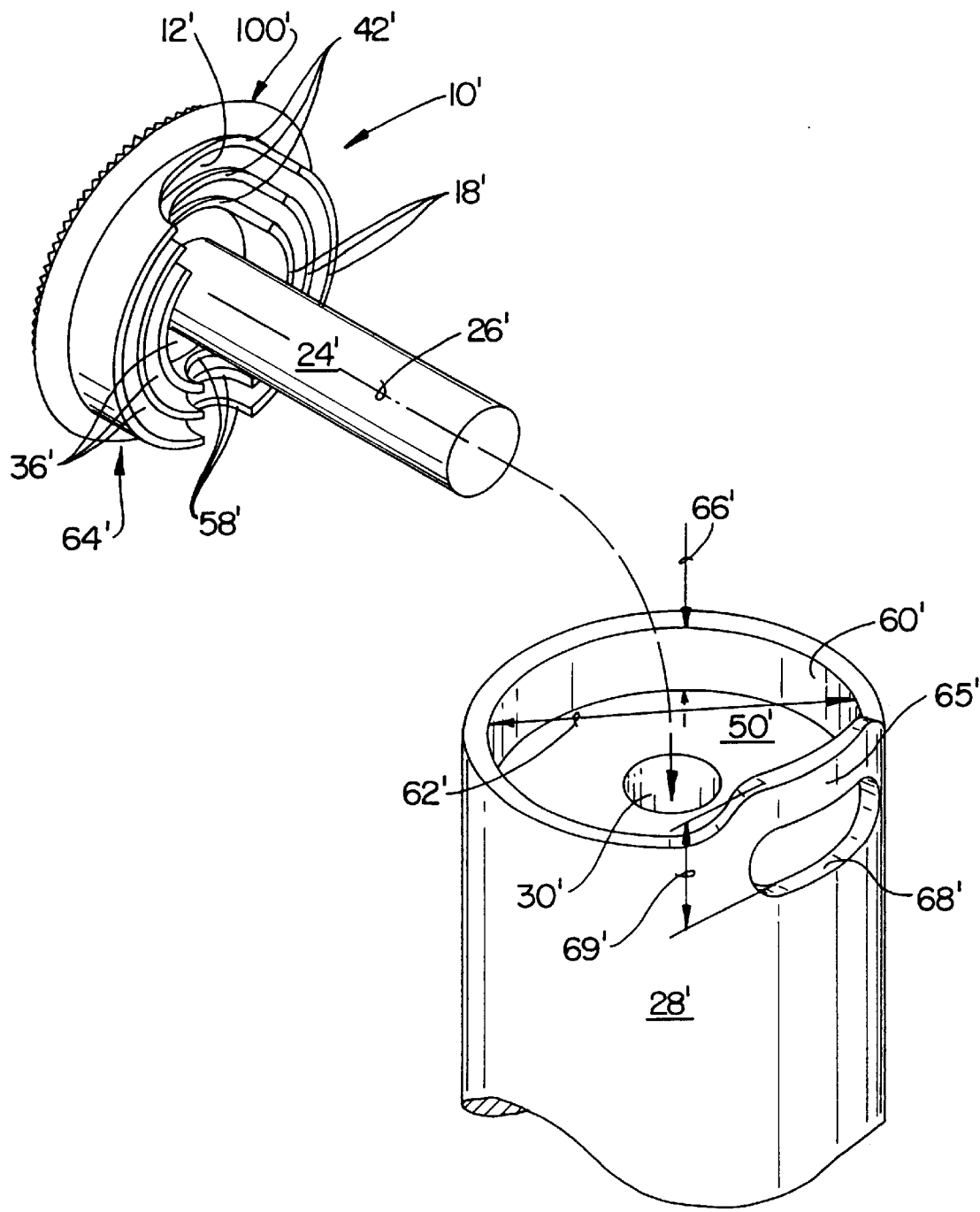
FIG. 6 is a perspective view of the preferred embodiment of the present invention and a chuck holder for use therewith.

The preferred embodiment of the chuck 10' of the present invention, along with the preferred chuck holder 28' is shown in FIG. 6. The preferred chuck 10' is same as the chuck 10 described above, except that each fin 18' of the preferred chuck 10' includes a second cut-out 58' opposite the first cut-out 42', and the first cut-out 42' of each fin 18' is substantially larger than the second cut-out 58' of each fin 18'. The second cut-out 58' of each fin 18' is radially aligned with the second cut-out 58' of each of the other fins 18' relative to the reference axis 26'.

The preferred chuck holder 28' is likewise similar to the chuck holder 28' described above except that the preferred chuck holder 28' further includes a circular lip 60' that extends up from the upper surface 50'. The inner diameter 62' of the lip 60' is a slightly smaller diameter than the outer diameter 64' of the O-ring 100', so as to provide a slight interference fit with the rubber (or neoprene) O-ring, and the lip 60' extends up from the upper surface 50' a height 66' that is sufficient to allow the base 12' of the chuck 10' to be positioned radially inward of the lip 60'. A finger hole (not shown) in the chuck holder 28', appropriately sized so as to permit insertion of a thumb or finger, intersects the bore 30' to provide access to the distal end of the-post 24' within the chuck holder 28' for the purpose of facilitating removal of the chuck 10' from the chuck holder 28' by pressing upwards on the distal end of the post 24'.

Figure 7:
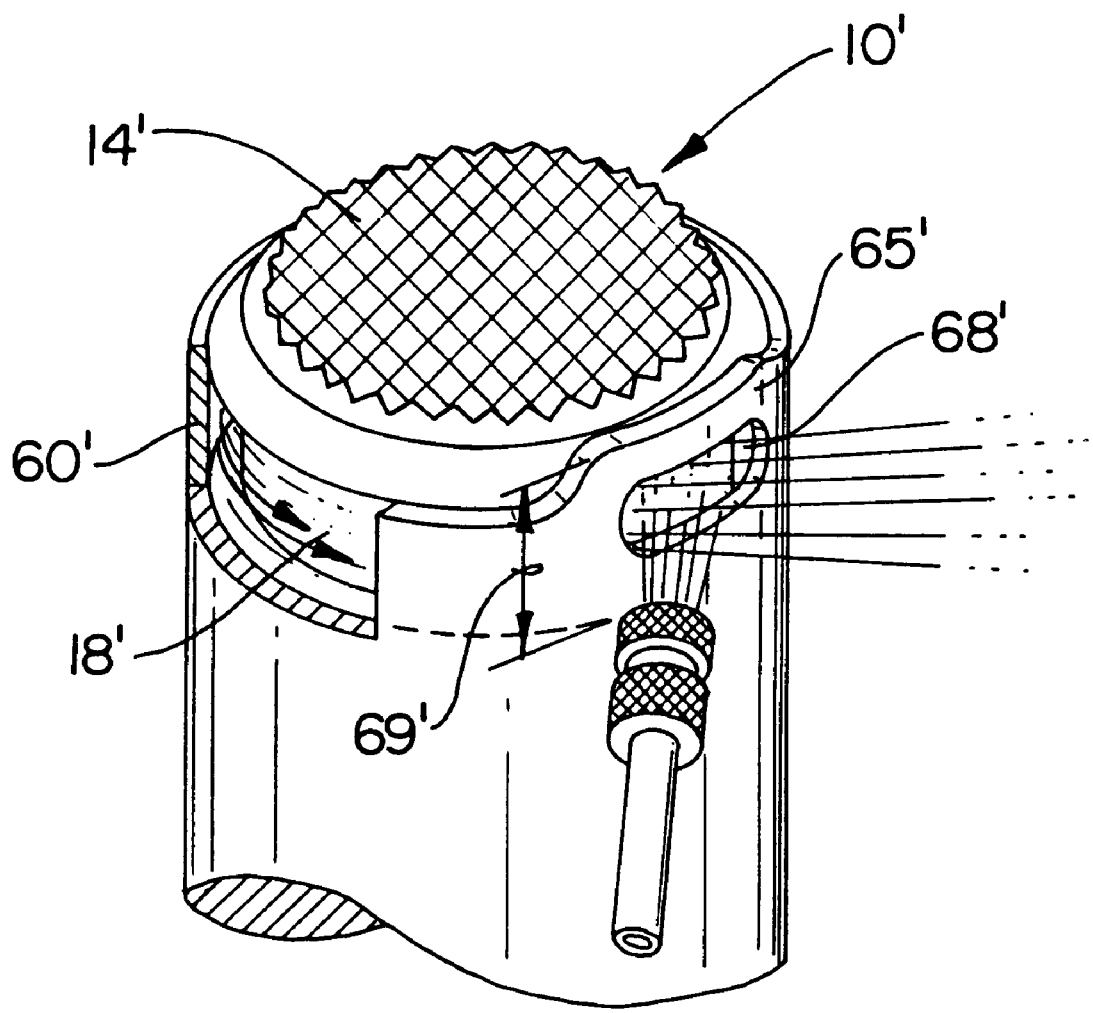
FIG. 7 is the perspective view of the chuck and chuck holder of FIG. 6, showing the introduction of coolant into the inlets of the channels of the preferred embodiment of the present invention.

As shown in FIG. 6, an orifice 68', which is properly sized to span the first cut-out 42' of each fin 18', extends through the lip 60'. The orifice 68' is slightly below the O-ring 100' when the chuck is positioned in the chuck holder 28'. The lip 60' includes a spray guard 65', that extends up from the upper surface 50' a height 69' that is essentially equal to the height 66' of the lip 60' plus the diameter of a cross-section of the O-ring 100', as shown in FIG. 7. The lip 60' and the radially outer fin 18' of the chuck 10' form an additional channel for the coolant 54' to flow through, and the second cut-outs 58' allow mixing between the channels 36'. This mixing results in faster and more uniform cooling of the tissue mounting surface 14' of the preferred chuck 10' as compared to the basic chuck 10. As those skilled in the art will readily appreciate, although the preferred embodiment of the present invention includes cut-outs 42, 58, incorporating these cut-outs 42, 58 likely results in a tissue chuck 28' that is more expensive to manufacture than if the fins 18' were continuous and uninterrupted by the cut-outs 42, 58. Obviously, if cost of manufacture is a significant consideration, the cut-outs 42, 58 can be eliminated from the tissue chuck 28' of the present invention if ramps (such as the one described herein in the second alternate embodiment of the present invention) are incorporated into the chuck holder 28' to provide for inflow and egress of the coolant 54' into the cooling channels 36'.

As shown in FIG. 8, the first alternate embodiment of the tissue chuck 10" of the present invention includes a base 12" having a tissue mounting surface 14" and a heat transfer surface 16". The chuck 10" is also preferably made of a material having high thermal conductivity, such as aluminum. Integral with the heat transfer surface 16" is a fin stem 17" extending in a first direction 20" away from the heat transfer surface 16" along a reference axis 26". The fin stem 17" includes a plurality of fins 19" that extend radially therefrom relative to the reference axis 26". Each fin 19" terminates in a fin end 21", and all of the fin ends 21" are preferably located the same distance 38" from the reference axis 26". The fin 19" furthest from- the base 12", is substantially thicker than the other fins 19", and supports most of the force exerted by the cryostat clamp (not shown) which is used to removeably secure the chuck 10" to the cryostat.

Referring again to FIG. 8, the base 12" is substantially circular and has an O-ring 100" seated in a groove (not shown) that extends about the circumference thereof. The base 12" includes a shoulder 13" adjacent the heat transfer surface 16" which results from the base 12" having an outer diameter that is a few millimeters greater than the outer diameter of the fins 19". Each fin 19" is essentially a disk that has its center located on the reference axis 26", and each fin 19" is in spaced relation to each adjacent fin 19", thereby defining channels 37" therebetween, and between the heat transfer surface 16" and the fin 19" closest the base 12". Each of the channels 37" preferably extend the same distance along the reference axis 26", and all of the fins 19" preferably have the same thickness except for the fin 19" furthest from the base 12", which is approximately three times thicker than the other fins 19" to support the force of the cryostat clamp as described above. As shown in FIG. 10, the tissue mounting surface 14" is essentially the same as that described for the preceding chucks 10, 10'.

As shown in FIG. 9, the chuck holder 28" comprises a piece of solid material, preferably a hard plastic, having a planar upper surface 50", with a circular lip 60" which terminates in a support surface 61". The inner diameter 62" of the lip 60" is approximately 5% larger than the outer diameter 65" of the fins 19", and the lip 60" extends up from the upper surface 50" a height 67" that is sufficient to prevent the distal end 25" of fin 19" stem 17" from contacting the upper surface 50" when the chuck 10" is positioned therein with the heat transfer surface 16" in contact with the support surface 61". Additionally, the inner diameter 62" of the lip 60" is approximately 5% smaller than the outer diameter 57" of the base 12", such that the base 12" cannot be positioned radially inward from the lip 60" (i.e. the base is a stop).

Figure 11:
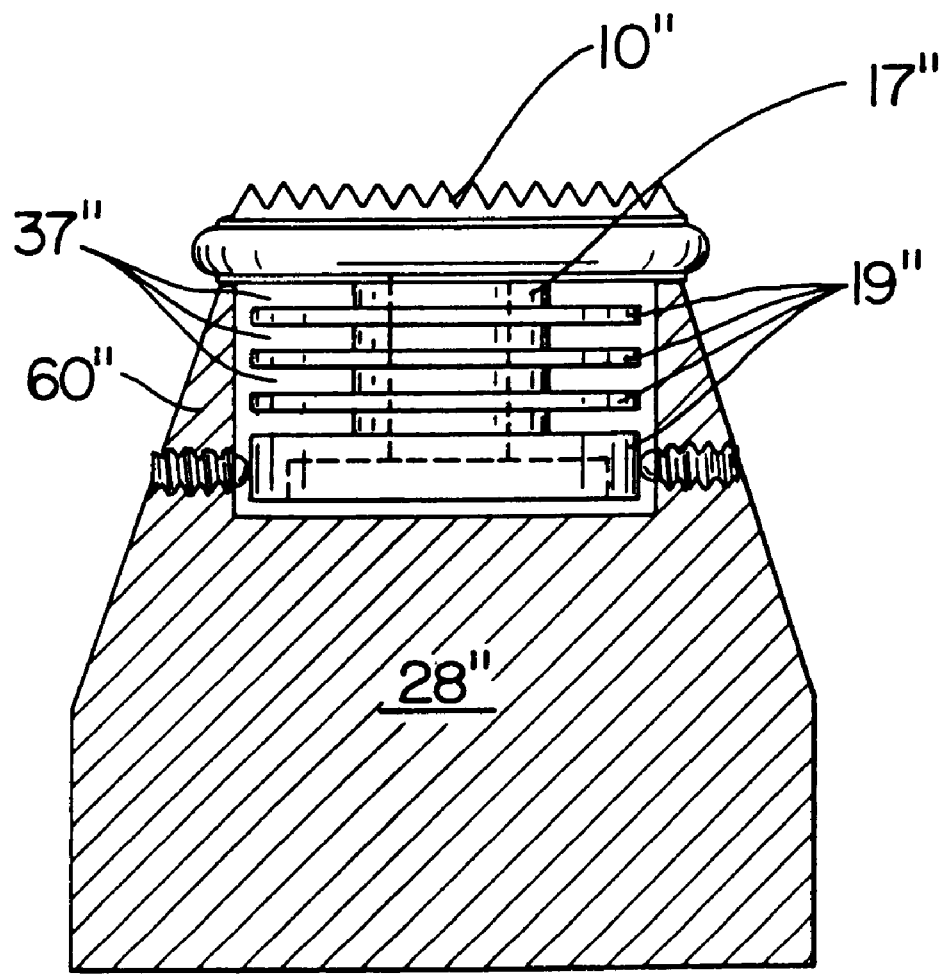
FIG. 11 is a cross-sectional view of the of the chuck and chuck holder of FIGS. 8 and 9, showing the fins of the chuck relative to the chuck holder.

As shown in FIG. 10, an orifice 68", which is properly sized to span from the heat transfer surface 16" to the fin 19" furthest from the base 12" when the chuck 10" is positioned therein, extends through the lip 60". As shown in FIG. 11, since each of the fins 19" extends the same distance from the fin stem 17", each of the fins 19" terminates short of the lip 60" when the chuck 10" is positioned into the chuck holder 28". This gap between the fins 19" and the lip 60" is for the purpose of allowing mixing between the channels 37". Because of the relatively large flow area provided by the channels 37", no spray guard is necessary on the chuck holder 28".

As shown in FIG. 10, when coolant 54", such as liquid nitrogen, is sprayed through the orifice 68" into the channels 37" to one side of the fin stem 17", the coolant 54" flows through each channel 37" and exits the chuck 10" through the orifice 68" as exhaust 56". As those skilled in the art will readily appreciate, as the coolant 54" passes through the channels 37", the coolant 54" absorbs heat from the fins 19" which in turn conduct heat, via the heat transfer surface 16", from the tissue mounting surface 14" of the base 12", causing rapid cooling of tissue mounting surface 14" as described above. Since this is accomplished without having to direct cooling spray directly onto the tissue sample (not shown), the problems associated with spraying coolant directly of the tissue sample are avoided entirely.

Figure 12:
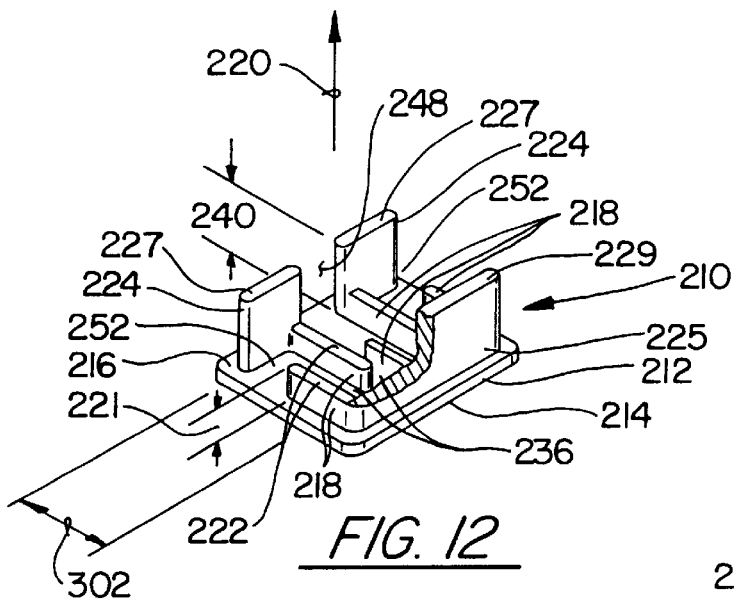
FIG. 12 is a perspective view of an second alternate embodiment of the present invention.

A second alternate embodiment of the present invention is shown in FIG. 12. The second alternate chuck 210 includes a base 212 that has a tissue mounting surface 214 and a heat transfer surface 216. The heat transfer surface 216 includes a plurality of fins 218, and two front walls 224 and one rear wall 225, each of which extends in a first direction 220 away from the heat transfer surface 216. Each fin 218 terminates in a fin end 222, and each fin end 222 is in spaced relation to the base 212. Each wall 224, 225 is integral with at least one of the fins 218, and the chuck 210 is likewise preferably made of a material having high thermal conductivity, such as aluminum.

Figure 14:
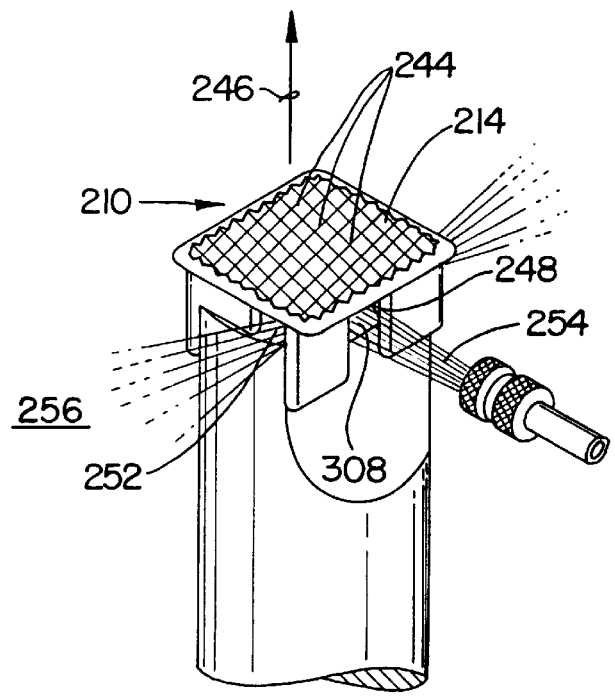
FIG. 14 is a perspective view of the present invention positioned within a chuck holder showing the introduction of coolant into the inlet of the channels of the second alternate embodiment of the present invention.

The base 212 is substantially rectangular and each fin 218 is preferably parallel, and in spaced relation to, each adjacent fin 218, defining channels 236 therebetween. As shown in FIG. 14, the tissue mounting surface 214 comprises a substantially planar surface having a plurality of protrusions 244 extending therefrom in a second direction 246 opposite the first direction 220. Walls 224, 225 that are integral with the base 212 extend in the first direction 220 away from the base 212.

Figure 13:
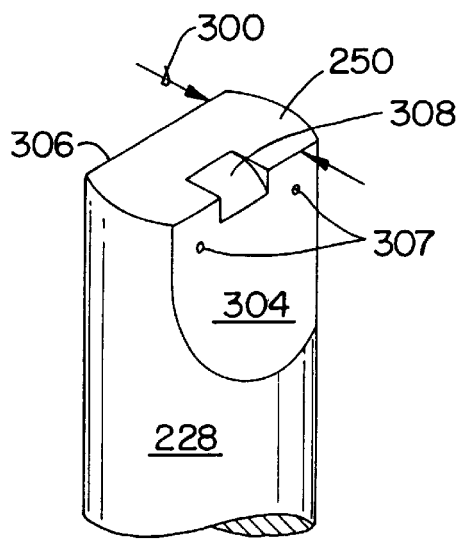
FIG. 13 is a view of a chuck holder for use with the second alternate embodiment.

The walls 224, 225 provide a means for removeably securing the chuck 210 to the chuck holder 228. As shown in FIG. 13, the chuck holder 228 comprises a piece of solid material having an upper surface 250 that has a width 300 that is essentially equal to the minimum distance 302 between wall 225 and either of the other walls 224. The chuck holder 228 has a front face 304 and a rear face 306, each of which include small detentes 307 extending slightly therefrom so as cause an interference fit with walls 224, 225 of the chuck 210 when it is positioned on the chuck holder 228 as shown in FIG. 14. A ramp 308, the purpose of which is described in greater detail below, extends between the upper surface 250 and the front face 304.

Each of the fin ends 222 is located a first predetermined distance 221 from the base 212, and each of the wall ends 227, 229 is located a second predetermined distance 240 from the base 212, and the second predetermined distance 240 is at least twice the first predetermined distance 221. Additionally, each fin 218 is preferably integral with only one wall 224, 225 and each fin 218 is preferably perpendicular to the walls 224, 225. The rear wall 225 is integral with at least three fins 218, and each fin 218 integral with a front wall 224 is interposed between the fins 218 that are integral with the rear wall 225. The front walls 224 are in spaced relation to each other, thereby defining an inlet 248 therebetween, and each of the front walls 224 is in spaced relation to at least one fin 218 that is integral with the back wall 225, thereby defining an outlet 252 therebetween.

Since each of the fins 218 extends the same distance 221 from the base 212, each of the fins 218 rests on the upper surface 250 when the chuck 210 is positioned into the chuck holder 228, such that the inlet 248 is positioned at the ramp 308. As shown is FIG. 14 when coolant 254, such as liquid nitrogen, is sprayed into the inlet 248 it is deflected by the ramp 308 into the channels 236. The coolant 254 flows then through each channel 236 to the outlet 252 thereof and exits the chuck 210 as exhaust 256. As those skilled in the art will readily appreciate as the coolant 254 passes through the tortuous channels 236, the coolant 254 absorbs heat from the fins 218 which in turn conduct heat from the tissue mounting surface 214 of the base 212. This causes rapid cooling of tissue mounting surface 214 at a rate which is sufficient to freeze most tissue samples while in plain view in a matter of seconds, without having to direct cooling spray directly onto the tissue sample (not shown). Thus, as in the case of the preferred embodiment, the problems associated with spraying coolant directly of the tissue sample are avoided entirely.

Although this invention has been shown and described with respect to detailed embodiments thereof, it will be understood by those skilled in the art that various changes in form and detail thereof may be made without departing from the spirit and scope of the claimed invention.

I claim:

1. A tissue chuck for use with a chuck holder for preparing a tissue sample for sectioning in a cryostat or the like, said chuck comprising:

a substantially circular base, said base having a heat transfer surface and a tissue mounting surface, and said tissue mounting surface is a substantially planar surface having a plurality of protrusions extending therefrom:

a plurality of fins extending in a first direction away from the heat transfer surface, each fin terminating in a fin end, and is each fin end is in spaced relation to said base, each fin is integral with said heat transfer surface, and each fin is annular, and in spaced relation to, each adjacent fin, defining channels therebetween; and, a post for removeably securing said chuck to said chuck holder, said post extending in said first direction away from said base along a reference axis, said post in spaced relation to each of said fins;

wherein said protrusions extend from said tissue mounting surface in a second direction opposite said first direction.

2. The chuck of claim 1 wherein each of said fins is coaxial with said post, each fin extends a first predetermined distance from said base, said post extends a second predetermined distance from said base, and said second predetermined distance is at least twice said first predetermined distance.

3. The chuck of claim 2 wherein each of said fins includes a first cut-out and a second cut-out, said first cut-out of each fin is substantially larger than said second cut-out of each fin, and said first cut-out of each fin is radially aligned with said first cut-out of each of said other fins relative to said reference axis.

4. The chuck of claim 3 wherein said second cut-out of each fin is radially aligned with said second cut-out of each of said other fins relative to said reference axis.

* * * * *